United States Patent [19] [11] 4,150,293

Franke [45] Apr. 17, 1979

[54] TOMOGRAPHIC APPARATUS FOR PRODUCING TRANSVERSE LAYER IMAGES

[75] Inventor: Kurt Franke, Erlangen, Fed. Rep. of Germany

[73] Assignee: Siemens Aktiengesellschaft, Berlin and Munich, Fed. Rep. of Germany

[21] Appl. No.: 779,671

[22] Filed: Mar. 21, 1977

[30] Foreign Application Priority Data

Apr. 1, 1976 [DE] Fed. Rep. of Germany ....... 2614083

[51] Int. Cl.² ............................................. G03B 41/16
[52] U.S. Cl. ................................. 250/445 T; 250/505
[58] Field of Search ..................... 250/445 T, 523, 505

[56] References Cited

U.S. PATENT DOCUMENTS

| 3,141,972 | 7/1964 | Oller | 250/523 |
|---|---|---|---|
| 3,549,885 | 12/1970 | Andersson | 250/523 |
| 3,944,833 | 3/1976 | Hounsfield | 250/445 T |
| 4,031,395 | 6/1977 | LeMay | 250/445 T |
| 4,057,725 | 11/1977 | Wagner | 250/445 T |

Primary Examiner—Craig E. Church
Attorney, Agent, or Firm—Hill, Gross, Simpson, Van Santen, Steadman, Chiara & Simpson

[57] ABSTRACT

In an illustrated embodiment a plurality of x-ray sources are arranged at equal angles about a rotating frame. Each source and detector arrangement may provide the desired number of measurements such as 240, so that the required angular movement for scanning is reduced by a factor corresponding to the number of sources. In one embodiment with three sources and 240 detectors for each source, the desired number of measured values may be obtained by rotation through 120 degrees instead of 360 degrees. In another illustrative embodiment, the narrow beam from the x-ray source covers about 30 detectors, the beam and detectors being linearly scanned so as to generate about 240 measurements, there being three source-detector arrangements separated by 60 degrees, so that scanning is carried out by rotation through 60 degrees rather than 180 degrees.

2 Claims, 2 Drawing Figures

TOMOGRAPHIC APPARATUS FOR PRODUCING TRANSVERSE LAYER IMAGES

BACKGROUND OF THE INVENTION

This invention relates to a tomographic apparatus for producing transversal layer images of a subject, comprising an x-ray measuring arrangement with a transmitting arrangement for emitting x-rays and a radiation receiver arrangement which determines the intensity of radiation behind the subject, and a drive system for the measuring arrangement with a rotating frame for producing rotational movements of the x-ray measuring arrangement, means being included for transforming the signals supplied by the ray receivers into a layer image.

A tomographic apparatus of this type is described in German Offenlegungsschrift No. 1,941,433. So far as the measuring arrangement is concerned, it is known from this particular publication to use a single x-ray tube and a single ray detector and to displace the measuring arrangement after each rotational movement through a small angle, along a straight line path perpendicular to the central ray of the x-ray beam to effect a scanning of the subject. In this known arrangement, therefore, rotational movements through small equal angles and linear scanning movements follow one another in an alternating sequence. However, it is also known that the displacement can be dispensed with, providing the ray receiver is made up of a plurality of ray detectors whose signals are simultaneously processed, and providing the x-ray beam is fan-shaped so as to strike all of the detectors simultaneously.

A disadvantage of the known tomographic apparatus is that the time required to build up an x-ray image is relatively long because the measuring arrangement has to be rotated through 180 degrees in the case where it is linearly displaceable, or through 360 degrees in the case where a row of detectors is used in conjunction with a fan-shaped x-ray beam.

SUMMARY OF THE INVENTION

The object of the present invention is to provide a tomographic apparatus of the type referred to above such that the time required to build up an x-ray image is considerably shortened in relation to the prior art.

According to the invention, this object is achieved by virtue of the fact that the transmitting arrangement comprises a plurality of x-ray sources with their focuses lying on a common circle and which are arranged offset at predetermined angles relative to one another and by virtue of the fact that one ray receiver is present for each x-ray source, the drive system for the rotating frame rotating the frame through an angle which corresponds to the number of x-ray tubes, for example. According to the invention, it is not necessary, for linear scanning of the subject in each angular position of the measuring arrangement, to rotate the measuring arrangement through 180 degrees about the patient. The linear movement can be obtained by means of a pinhole diaphragm and a displaceable detector, as will be explained hereinafter. In cases where a fan-shaped x-ray beam is used in conjunction with a row of detectors for each x-ray source, the angle of rotation may be smaller than 360 degrees, that is smaller than in the prior art for a given desired total number of measurement values. Accordingly, the time required to build up an x-ray image is considerably shortened in relation to the prior art.

Other objects, features and advantages of the invention will be apparent from the following detailed description taken in connection with the accompanying sheet of drawings.

DESCRIPTION OF THE PREFERRED EMBODIMENTS

Two embodiments of the invention are described by way of example in the following, having reference to FIGS. 1 and 2 of the accompanying drawings.

Figure 1:
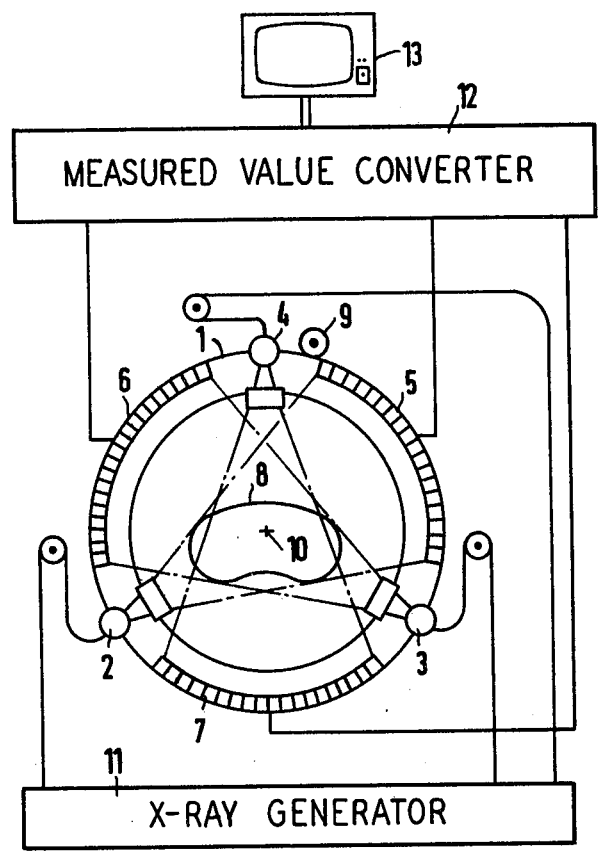
FIG. 1 is a somewhat diagrammatic view illustrating a first embodiment in accordance with the present invention.

FIG. 1 shows a rotating frame 1 on which three x-ray tubes 2, 3 and 4 are mounted, the tubes being offset at angles of 120 degrees relative to one another. A ray receiver is arranged opposite each of the x-ray tubes 2-4. These ray receivers are designated by reference numerals 5, 6 and 7. Each of the x-ray tubes 2-4 emits a fan-shaped x-ray beam having an extent longitudinally of the axis of subject 8 which is equal to the selected layer thickness, and having a width such that on the one hand, the entire subject is covered, while on the other hand the radiation only strikes the associated ray receiver. The rotating frame 1 is rotatable about the center point 10 which is intended substantially to coincide with the center point of the subject 8, by means of a diagrammatically illustrated drive system 9. The x-ray tubes 2-4 are connected to an x-ray generator 11, and the detectors 5-7 deliver their signals to a transducer means which builds up an x-ray image from the signals and effects its reproduction on a display unit 13, for example.

For completely scanning the subject 8, the rotating frame 1 with components 2-7 merely has to be rotated through an angle of 120 degrees by means of the drive system 9. Accordingly, the time required to build up an x-ray image is reduced by one third as compared with the known tomographic apparatus mentioned at the outset.

Figure 2:
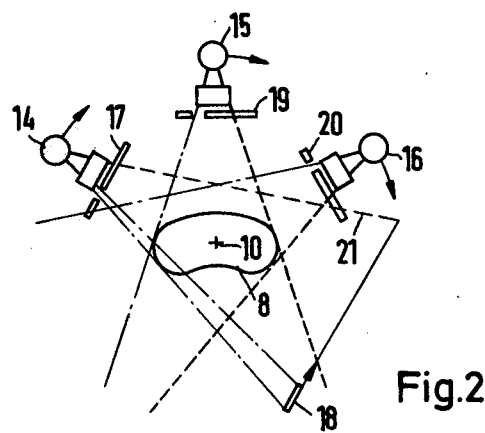
FIG. 2 is a diagrammatic view similar to FIG. 1 but illustrating a second embodiment in accordance with the present invention.

In the embodiment illustrated in FIG. 2, three x-ray tubes 14, 15 and 16, are shown each of which having an adjustable lead (Pb) pinhole diaphragm and an adjustable ray receiver, these parts being arranged on a rotating frame (not shown) which corresponds to the rotating frame 1 of FIG. 1. In the interest of clarity, FIG. 2 only shows the ray receiver 18 of the x-ray tube 14 in conjunction with a lead pinhole diaphragm 17. The lead pinhole diaphragm 17 and the corresponding lead pinhole diaphragms 19 and 20 of the x-ray tubes 15 and 16 condense or define the x-rays into narrow x-ray beams which strike the ray receiver 18 and the corresponding receivers of the x-ray tubes 15 and 16, each beam being confined to impingement on its associated receiver only. In a specific position of the x-ray tubes 14-16, the lead pinhole diaphragms 17, 19, 20 and the corresponding ray receivers are moved synchronously with one another parallel to a tangent of the circle of rotation of the x-ray tubes 14-16 in such a way that the entire subject 8 is scanned. Thus, for example, the receiver 18 and the lead pinhole diaphragm 17 are moved until they reach a position indicated by the dash line 21. The subject 8 is thereby scanned, after which the lead pinhole diaphragms and the ray receivers are moved back into their starting positions which are shown in FIG. 2. Thereafter the x-ray tubes 14–16, the lead pinhole diaphragms 17, 19, 20 and all the ray receivers are rotated together through a predetermined angle, for example one degree (1°) and another scanning operation effected. This scanning operation is also followed by a rotation, and the scannings and rotations follow one another until the x-ray tube 14 occupies the position of the x-ray tube 15, for example. By this time, the subject 8 has been scanned sixty times by each of three different x-ray beams, this corresponding to 180 of the conventional scanning operations with a single fan-shaped beam. Where the ray receiver 18 comprises thirty detector elements, for example, and the length of the ray receiver 18 is equivalent to one eighth of the distance traveled by the ray receiver 18 during a single scanning operation, 240 measured values are obtained during a single scanning, so that a total of 240×180=43,200 measured values are obtained for the rotational movement of all of the x-ray tubes 14–16 with the associated lead pinhole diaphragms 17, 19 and 20 and the ray receivers such as 18.

The embodiment illustrated by way of example in FIG. 2 corresponds to a measuring arrangement with an x-ray tube and a ray receiver in which this measuring arrangement is rotated through 180 degrees about the patient. Accordingly, the x-ray tubes 14–16 are offset at angles of 60 degrees relative to one another. By contrast, the embodiment illustrated by way of example in FIG. 1 corresponds to an arrangement with an x-ray tube and a ray receiver which is rotated through 360 degrees about the patient. Accordingly, the x-ray tube 2, 3, 4 are offset at angles of 120° relative to one another. In the embodiment illustrated in FIG. 2, the angle of rotation is 60 degrees, while in the embodiment illustrated in FIG. 1, it is 120 degrees.

If the apparatus shown in FIG. 1 is compared with the apparatus shown in FIG. 2, it can be seen that, when 240 measured values are supplied during each scanning operation of the apparatus shown in FIG. 2, the ray receivers 5, 6, 7 of FIG. 1 would have to consist of 240 individual detectors in a corresponding embodiment of the apparatus shown in FIG. 1. However, an embodiment such as this is complicated and expensive to manufacture. By contrast, the embodiment illustrated by way of example in FIG. 2 manages with only thirty individual detectors for one ray receiver. Although the examination time is somewhat longer than in the embodiment illustrated in FIG. 1, the ray receivers are simpler in structure. The embodiment illustrated by way of example in FIG. 1 can also be built up in accordance with the embodiment illustrated by way of example in FIG. 2 and, conversely, the embodiment illustrated by way of example in FIG. 2 can be built up in accordance with the embodiment illustrated by way of example in FIG. 1. Thus, x-ray sources 2, 3 and 4 may be offset at 60 degrees relative to one another and the receivers 5, 6 and 7 correspondingly may have a circumferential extent of approximately 60 degrees, or the sources 14, 17; 15, 19; and 16, 20 of FIG. 2 may have a spacing of 120 degrees, with the receivers such as 18 traversing an arc of approximately 120 degrees. The particular angular relationships selected depend upon whether it is desired to conduct an examination of the patient which corresponds to rotation of the measuring arrangement through 180 degrees or 360 degrees, for example.

Within the framework of the invention, a reduction in the image-formation time as compared with the prior art is already possible by using two x-ray tubes in conjunction with two ray receivers, but it is also possible to use more than three x-ray sources in conjunction with a corresponding number of ray receivers. Finally, it is also possible, in cases where a single detector is used for each x-ray tube, fixedly to arrange the x-ray tube in relation to the rotating frame and to determine the direction of the x-ray beam by means of a displaceable mask or by electronic means.

It will be apparent that many further modifications and variations may be effected without departing from the scope of the novel concepts and teachings of the present invention.

I claim as my invention:

1. A tomographic apparatus for producing transversal layer images of a subject, consisting of an x-ray measuring arrangement with a transmitting arrangement for emitting x-rays and with radiation receivers which determine the intensity of radiation behind the subject by scanning the x-rays, and of a drive system for the measuring arrangement with a rotating frame for producing rotational movements of the x-ray measuring arrangement, the transmitting arrangement comprising a plurality of x-ray tubes with their focuses lying substantially on a common circle, and arranged offset at predetermined angles relative to one another, one ray receiver being provided for each x-ray tube, the x-ray tubes being fixedly mounted on the rotating frame and having pinhole diaphragms for condensing the x-ray beam in such a way that it impinges on the ray receivers, said diaphragms being mounted for movement parallel to a tangent of the circle of rotation of the x-ray tubes and the radiation receivers being mounted for movement parallel to the path of the diaphragm such that the x-ray beam always strikes the ray receivers during movement thereof in the scanning of the subject, the ray receivers each consisting of a row of detectors movable as a group parallel to a tangent of the circle of rotation of the x-ray tubes, all of the detectors of each row being simultaneously impinged by the respective x-ray beam in each position of the respective diaphragm during each cycle of tangential movement of the diaphragms, and the rows of detectors all moving tangentially synchronously with the movement of the respective pinhole diaphragms during each cycle of tangential movement of the diaphragms, whereby all the detectors of all of the rows are used substantially simultaneously while the rows of detectors each cover only a fraction of the length of the tangential path along which the respective x-ray beam is moved during each cycle of tangential movement of the respective diaphragm.

2. Apparatus according to claim 1, wherein each row of detectors comprises about thirty individual detectors.

* * * * *